United States Patent
Tichy et al.

(10) Patent No.: US 11,950,927 B2
(45) Date of Patent: Apr. 9, 2024

(54) DENTAL OBJECT FOR ATTACHING TO A TOOTH

(71) Applicant: Ivoclar Vivadent AG, Schaan (LI)

(72) Inventors: Raimund Tichy, Feldkirch (AT); Jonas Reinhardt, Igis (CH)

(73) Assignee: Ivoclar Vivadent AG, Schaan. (LI)

( * ) Notice: Subject to any disclaimer, the term of this patent is extended or adjusted under 35 U.S.C. 154(b) by 0 days.

(21) Appl. No.: 17/541,629

(22) Filed: Dec. 3, 2021

(65) Prior Publication Data
US 2022/0183623 A1   Jun. 16, 2022

(30) Foreign Application Priority Data
Dec. 16, 2020 (EP) .................................... 20214675

(51) Int. Cl.
*A61B 5/00* (2006.01)

(52) U.S. Cl.
CPC .................................. *A61B 5/682* (2013.01)

(58) Field of Classification Search
CPC ..... A61B 5/682; A61B 5/6801; A61B 5/6813; A61B 5/6814; A61B 5/68; A61C 7/12; A61C 7/14; A61C 7/145; A61C 7/16; A61C 7/28; A61C 19/04; A61C 13/225; A61C 13/2255; A61C 13/24; A61C 5/30; A61C 5/682
See application file for complete search history.

(56) References Cited

U.S. PATENT DOCUMENTS

| | | | | |
|---|---|---|---|---|
| 454,566 A | * | 6/1891 | Land | A61C 5/00 433/226 |
| 713,273 A | * | 11/1902 | Alexander | A61C 5/85 433/40 |
| 1,384,282 A | * | 7/1921 | Tuttle | A61C 13/1006 433/225 |
| 4,526,544 A | * | 7/1985 | Kahn | A61C 5/50 523/117 |
| 4,571,188 A | * | 2/1986 | Hamilton | A61C 5/80 433/226 |
| 4,632,977 A | * | 12/1986 | Riazi | B29B 13/00 264/16 |
| 5,415,547 A | * | 5/1995 | Torabinejad | A61K 6/851 433/224 |
| 2002/0123024 A1 | | 9/2002 | Jensen et al. | |
| 2002/0177100 A1 | | 11/2002 | Jensen et al. | |
| 2003/0148247 A1 | * | 8/2003 | Sicurelli, Jr. | A61C 13/30 433/224 |
| 2003/0165792 A1 | * | 9/2003 | Jodaikin | A61P 1/02 433/80 |
| 2003/0199605 A1 | | 10/2003 | Fischer | |
| 2004/0038178 A1 | * | 2/2004 | Mayer | A61C 5/73 433/226 |

(Continued)

FOREIGN PATENT DOCUMENTS

WO   03096922 A1   11/2003

*Primary Examiner* — Cris L. Rodriguez
*Assistant Examiner* — Kylie M. Gaspar
(74) *Attorney, Agent, or Firm* — Ann M. Knab; Thad McMurray

(57) ABSTRACT

The present invention relates to a dental object (100) for attaching to a tooth (101) or teeth in an intraoral space, having an adhesive region (103) with a gutta-percha material (105) for attaching the dental object (100) to the tooth (101) or teeth.

11 Claims, 3 Drawing Sheets

(56) References Cited

U.S. PATENT DOCUMENTS

| | | | |
|---|---|---|---|
| 2004/0158194 A1* | 8/2004 | Wolff | A61J 7/0092 604/66 |
| 2004/0209229 A1 | 10/2004 | Jensen et al. | |
| 2005/0196729 A1* | 9/2005 | Jessop | A61C 19/06 433/80 |
| 2008/0026344 A1 | 1/2008 | Uji | |
| 2008/0118882 A1* | 5/2008 | Su | A61K 6/30 523/105 |
| 2008/0206716 A1* | 8/2008 | Asgary | A61P 1/02 433/228.1 |
| 2008/0299513 A1* | 12/2008 | Jia | A61K 6/54 433/81 |
| 2009/0286195 A1* | 11/2009 | Sears | A61C 7/14 433/18 |
| 2011/0123959 A1 | 5/2011 | Sicurelli et al. | |
| 2011/0182995 A1 | 7/2011 | Asgary | |
| 2011/0212406 A1* | 9/2011 | Jensen | A61C 7/14 433/9 |
| 2013/0040267 A1 | 2/2013 | Bergheim | |
| 2013/0196281 A1* | 8/2013 | Thornton | A61C 19/063 433/8 |
| 2014/0121280 A1 | 5/2014 | Primus et al. | |
| 2015/0170504 A1* | 6/2015 | Jooste | A61B 5/6802 340/539.12 |
| 2015/0173852 A1* | 6/2015 | Khakpour | A61C 1/0046 433/215 |
| 2015/0216641 A1* | 8/2015 | Popa-Simil | A61C 19/04 433/8 |
| 2016/0038380 A1 | 2/2016 | Primus et al. | |
| 2016/0136058 A1* | 5/2016 | Schlüter | A61K 6/54 424/78.37 |
| 2019/0110864 A1* | 4/2019 | Clunet-Coste | A61C 5/50 |
| 2019/0167386 A1* | 6/2019 | Raghavan | A61B 5/14542 |
| 2020/0188062 A1* | 6/2020 | Kopelman | A61C 7/08 |
| 2021/0282650 A1 | 9/2021 | Yoshida et al. | |
| 2021/0315460 A1 | 10/2021 | Hazama et al. | |
| 2021/0346690 A1 | 11/2021 | Demarest et al. | |
| 2021/0353180 A1 | 11/2021 | Fischer et al. | |

* cited by examiner

DENTAL OBJECT FOR ATTACHING TO A TOOTH

CROSS-REFERENCE TO RELATED APPLICATIONS

This application claims priority to European Patent Application No. 20214675.9 filed on Dec. 16, 2020, the disclosure of which is incorporated herein by reference in its entirety.

TECHNICAL FIELD

The present invention relates to a dental object for attachment to a tooth or teeth and a method for attaching a dental object to a tooth or teeth.

BACKGROUND

Today's intraoral fixation options are realized by mechanical clamps or chemically by bonding (adhesion). Known clamping methods include, for example, clamps that are placed around one or more teeth, dental aligners that encompass all or part of an arch, or molar bands that are placed around one or more teeth.

Adhesion of foreign bodies is achieved by means of adhesives or cements. Another reversible option for attachment is suction by means of adhesive cream. However, this only works on the gum, not on the tooth itself. Moreover, the bonding cream only works on larger surfaces. Further, modern adhesive creams provide only weak attachment, making it impossible to wear a swallowable foreign body overnight.

U.S. 20080026344, 20210353180, 20210346690, 20210315460, and 20210282650 are directed to sensors for use in the oral cavity and are hereby incorporated by reference in their entirety. U.S. 20110123959, 20160038380, 20140121280, 20130040267, 20110182995, 20080206716, 20040209229, 20030199605, 20020177100 and 20020123024 are directed to the use of gutta percha in the dental industry and are hereby incorporated by reference in their entirety.

SUMMARY

Therefore, it is the technical problem of the present invention to firmly yet removably attach a dental object to a tooth or teeth.

This problem is solved by subject-matter according to the independent claims. Technically advantageous embodiments are the subject of the dependent claims, the description, and the drawings.

According to a first aspect, the technical problem is solved by a dental object for attachment to a tooth or teeth in an intraoral space, with an adhesive region comprising gutta-percha for attaching the dental object to the tooth or teeth. This provides the technical advantage that the patient can remove and reinsert the dental object at any time. The removability allows plaque build-up under or around the dental object to be cleaned after removal. The dental object can be attached lingually, labially, buccally, or at other locations on the tooth. Teeth are not damaged by the dental object because no etching, clamps, brackets, or metal are used. Teeth are not displaced, such as with a molar band, and no bonding cream is needed.

In a technically advantageous embodiment of the dental object, the dental object comprises a housing and/or a retaining plate. The housing can be made of plastic or metal, for example. This has, for example, the technical advantage that further components can be arranged in the housing.

In a further technically advantageous embodiment of the dental object, a layer of the gutta-percha material is attached to the housing. This provides, for example, the technical advantage that the housing can be attached directly to the tooth.

In a further technically advantageous embodiment of the dental object, the layer of gutta-percha material is attached to the housing by means of an adhesive layer. The housing may comprise a textured surface for attaching the gutta-percha material. The housing may include one or more latching elements for attaching the gutta-percha material. The housing may include one or more connecting elements for creating a form fit between an adhesive region and the sensor or sensor housing. The adhesive layer and the other bonding and latching elements cause a strong bond between the housing and the gutta-percha material. The housing may also have a structured contact surface or openings into which the gutta-percha material is embedded. This provides, for example, the technical advantage of preventing detachment of the gutta-percha material from the housing.

In a further technically advantageous embodiment of the dental object, the layer of gutta-percha material has a thickness of 1 μm to 5 mm. This has, for example, the technical advantage that good adhesion of the dental object is achieved and individual adaptation for each patient is possible.

In a further technically advantageous embodiment of the dental object, the gutta-percha material comprises a prefabricated passage opening for guiding liquid from the tooth into the interior of the housing. This provides, for example, the technical advantage that saliva inside the housing can be analyzed by a sensor.

In a further technically advantageous embodiment of the dental object, the gutta-percha material comprises antibacterial particles or substances. This provides, for example, the technical advantage of preventing bacterial infections when the dental object is worn. The gutta-percha material may also comprise substances that locally regulate the pH value so that caries cannot develop.

In a further technically advantageous embodiment of the dental object, the gutta-percha material comprises a plasticizer. The plasticizer may comprise, for example, medium-chain triglycerides (miglyol), glycerol or other fats, such as olive oil. This provides, for example, the technical advantage of allowing the bonding region to better conform to the tooth.

In a further technically advantageous embodiment of the dental object, the gutta-percha material, the sensor and/or the housing comprises one or more channels for guiding saliva to a sensor unit. The channels are formed, for example, by recesses. The channels may be provided for passing fluid therethrough. This provides, for example, the technical advantage of promoting fluid passage in the contact region.

In a further technically advantageous embodiment of the dental object, the channels extend obliquely or vertically through the gutta-percha material, the sensor and/or the housing. This provides, for example, the technical advantage of generating saliva flow towards a sensor unit.

In a further technically advantageous embodiment of the dental object, the gutta-percha material is anatomically preformed. This has, for example, the technical advantage that a faster adaptation of the adhesive region takes place.

In a further technically advantageous embodiment of the dental object, the dental object comprises a sensor, an electronic component, and/or a battery. For example, the dental object comprises electronics and a transmitter, such as NFC circuitry, or Bluetooth™ wireless connection. This provides, for example, the technical advantage that data can be obtained and processed by the dental object.

According to a second aspect, the technical problem is solved by a method for attaching a dental object to a tooth or teeth, comprising the step of pressing an adhesive region of the dental object comprising gutta-percha material onto the tooth. The method has the same technical advantages as the dental object according to the first aspect.

In a technically advantageous embodiment of the method, the gutta-percha material is heated before the adhesive region is pressed on. This has, for example, the technical advantage that the adhesive region adapts better to the tooth and a strong bonding effect is achieved.

According to a third aspect, the technical problem is solved by using gutta-percha to attach a dental object to a tooth or teeth. The use has the same technical advantages as the dental object according to the first aspect.

BRIEF DESCRIPTION OF THE DRAWINGS

Examples of embodiments of the invention are shown in the drawings and are described in more detail below.

It shows.

DETAILED DESCRIPTION

Figure 1:
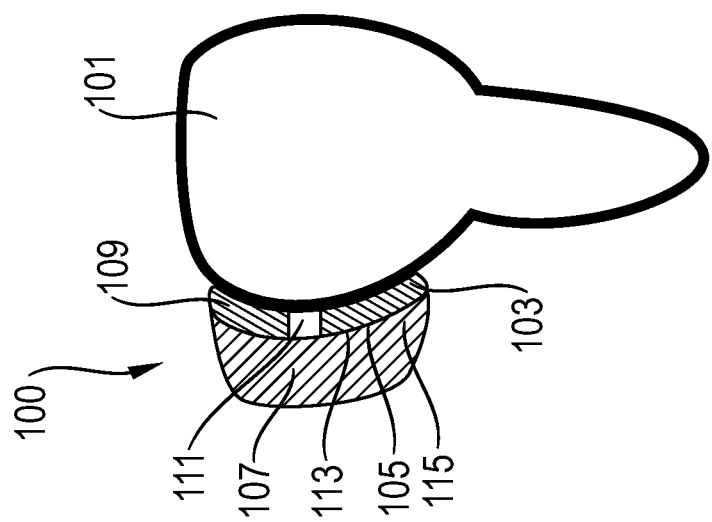
FIG. 1 a schematic view of a dental object.

FIG. 1 shows a schematic view of a dental object 100 for attachment to a tooth 101. The dental object 100 has an adhesive region 103 comprising Gutta Percha material 105 for attaching the dental object 100 to the tooth 101. The plastic adhesive region 103 is pressed onto the tooth 101 for attachment. For this purpose, the gutta-percha material 105 can be heated, for example, with a hot air source or in a water bath, and inserted into a patient's mouth in a heated state (~50° C.). The gutta-percha material 105 bonds to the tooth 101 and gums while cooling to mouth temperature, so that the dental object 100 is molded and fixed in the mouth. The gutta-percha material 105 creates an adhesive effect to the tooth 101.

The gutta-percha material 105 is a plastic, rubbery, caoutchouc-like material derived from the dried, coagulated milky sap of sapotaceous plants (*Sapotaceae*) (*Payena* spp. and *Palaquium* spp.) and spindle bushes (*Euonymus* spp.) or the gutta-percha tree (*Palaquium gutta*). Gutta-percha material 105 includes gutta-percha. Gutta-percha has the following molecular structure in which the number n of repeat units is typically in the range of 100. The gutta-percha is non-crosslinked. Gutta-percha exhibits high biocompatibility, dimensional stability and plastic deformability.

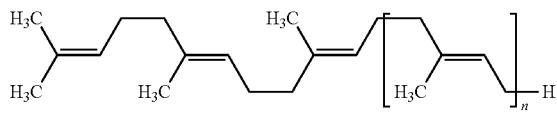

The dental object 100 with the adhesive region 103 made of gutta-percha material 105 has the technical advantage that non-prosthetic and non-orthodontic dental objects 100 can be removably attached in the intraoral area.

The dental object 100 may include: sensors, electronic components, batteries, or housings for various components. The housing 107 may be made of a plastic, carbon, or metal. The dental object 100 may be an object that already has a shape that is anatomically adapted to the tooth 101. For example, such an object may be individually created using a 3D-printer and adapted to the specific shape of a tooth 101 of a patient, such as an individually shaped dental attachment. In general, the dental object 100 may be any object that is to be attached to the tooth 101 in the oral cavity.

The gutta-percha material 105 may be arranged in a layer 109 as an adhesive area 103 on the dental object 100. The layer 109 has a thickness of 1 μm to 5 mm, for example. The dental object 100 and/or the adhesive region 103 may be anatomically preformed in that they comprise a concave indentation 113 in which the tooth 101 lies. Several concavities 113 can also be provided, in each of which a tooth 101 is then located.

As a result, the dental object 100 fits more snugly against the tooth 101. A prefabricated passageway 111 may be provided in the layer 109 for guiding fluid from the tooth to the interior of the housing 107. This allows the fluid from the tooth 101 inside the housing 107 to be analyzed by a sensor.

The gutta-percha material 105 may comprise antibacterial particles, such as by an incorporation of silver particles, copper particles, or a mixture with chlorhexidine and chloroxylenol. In addition, the plastic material or gutta-perha material may comprise antibiotics, such as penicillin, clindamycin, erythromycin, cefadroxil, metronidazole, and/or tetracyclines. In addition, pH-regulating filler materials may be used, such as calcium fluoride, calcium hydroxide, or alkaline glass fillers, such as calcium fluorosilicate glass or ion-releasing materials, such as those of F—, OH—, or Ca2+.

For customized dental objects 100 that are spatially and anatomically adapted to the tooth 101, the thickness of the layer 109 may be small and in the range of 200 μm. In prefabricated, standard dental objects 100, the thickness of the layer 109 is in the range of millimeters, since greater plastic deformation of the layer 109 takes place. For example, the dimensions of the layer 109 in length and width may be 10 mm by 10 mm. However, in general, other dimensions may be selected if convenient.

Due to the attachment with the gutta-percha material 105, the dental object 100 can be removed at any time and reinserted after heating. Even a moist environment (saliva) does not pose a problem, as the Gutta-Percha material 105 does not dissolve in water. In addition, Gutta-Percha is biocompatible.

The cementation of the dental object 100 with the Gutta-percha material is stronger than with other common materials. As a result, reversible attachment of the dental object 100 in the intraoral space can be achieved. The gutta-percha material 105 is used as an agent in this case. The advantage of the gutta-percha material 105 is that it can also be used on curved surfaces. The connection can be used several times after brief heating before reinsertion. The connection is gentle on the teeth, as no etching of the tooth structure is required. Heating of the gutta-percha material can be performed again to facilitate removal.

Heating or warming of the gutta-percha material 105 prior to pressing on the dental object 100 may be accomplished using a hot air blower or a water bath. However, the dental object 100 may also include an electrical or chemical heating device that is activated by a user during insertion of the dental object 100. For example, the electrical heating device may be formed by a heating coil. The chemical heating device may be formed by two substances that are reacted together to generate heat for the gutta-percha material 105. Through the heating device, the gutta-percha material 105 is automatically heated to the desired temperature by the dental object 100 without the need for any other devices. For example, the gutta-percha material 105 is thereby raised to a temperature of 40°-80° C.

The dental objects 100 prepared with the gutta-percha material 105 can be heated, for example, by means of a hot air stream of 110-130° C. for approx. 1 to 2 min. The surface temperature of the gutta-percha material 105 should not exceed 45-50° C. so as not to cause any injuries to the gums or irritations on the teeth later on the patient. The dental object 100 is then pressed onto the tooth by hand and can then be cooled with a stream of cool air so that it retains its shape. The gutta-percha material 105 is also automatically cooled within a few minutes by the flow of saliva and blood in the teeth.

The dental object 100 provides a strong, easily reversible attachment in the intraoral space. The detachability and simplicity of the fixation by the patients is particularly advantageous, so that they can perform their usual oral hygiene and no secondary diseases are triggered by the dental object 100. The gutta-percha material 105 serves as a shaping element and as a bonding agent for the flexible attachment. For better bonding to the gutta-percha material 105, the tooth inner side of the housing 107 may be roughened by sandblasting and/or may comprise an adhesive layer 115. The adhesive layer 115 may be created using adhesive bonding methods or spray adhesive, for example. However, the housing 107 may also comprise one or more latching elements or connecting elements for creating a positive fit between the adhesive region and the sensor or sensor housing. For example, the connecting element may be formed by one or more nubs.

Figure 2:
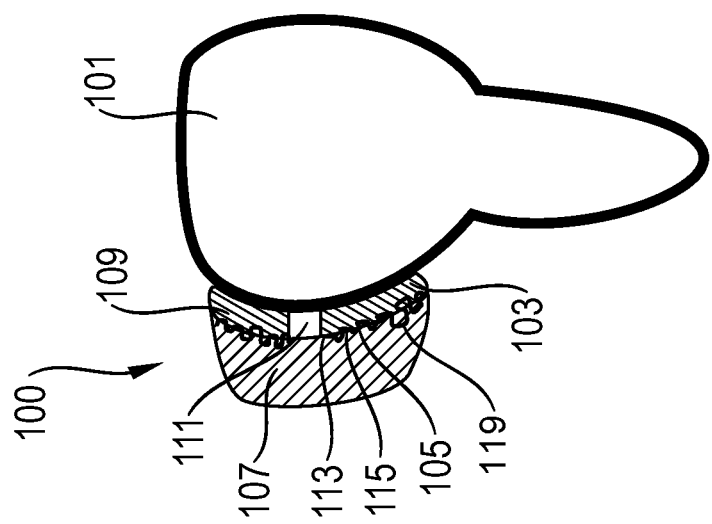
FIG. 2 a further schematic view of a dental object.

FIG. 2 shows another schematic view of a dental object 100. The dental object 100 has a structured contact surface 119 with recesses or openings in which the gutta-percha material 105 is located. The textured contact surface 119 provides a greater surface area, thereby increasing the adhesion of the gutta-percha material 105 to the dental object 100. The dental object 100 may also include latching elements or fasteners for securing the gutta-percha material 105.

Figure 3:
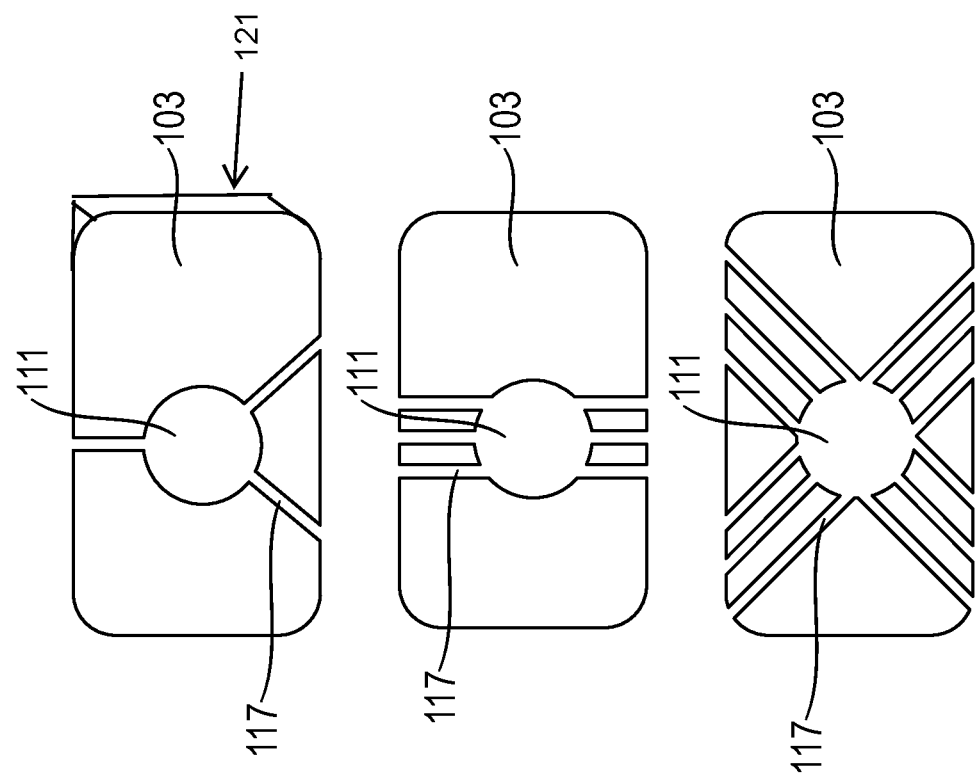
FIG. 3 a schematic view of a plastic attachment region.

FIG. 3 shows a schematic view of the plastic adhesion region 103 with channels 117 for a liquid outflow or an air supply having a retaining plate 121. In the adhesion area 103 with the gutta-percha material 105, the through opening 111 for enabling a measurement by a sensor unit is arranged. The through opening 111 forms a measurement area for the sensor unit.

The channels 117 are formed in the adhesion area 103 by recesses and serve to supply liquid (saliva) to the sensor unit or to enable ventilation of the measuring area. The channels 117 can be arranged in horizontal, diagonal or vertical direction.

All features explained and shown in connection with individual embodiments of the invention may be provided in different combinations in the subject matter of the invention to simultaneously realize their beneficial effects.

All method steps can be implemented by devices which are suitable for executing the respective method step. All functions that are executed by the features in question can be a method step of a method.

The scope of protection of the present invention is given by the claims and is not limited by the features explained in the description or shown in the figures.

REFERENCE LIST

100 Dental object
101 Tooth
103 Adhesive region
105 Gutta-percha Material
107 Housing
109 Layer
111 Passage opening
113 Arches
115 Adhesive layer
117 Channel
119 Contact area

The invention claimed is:

1. A dental object (100) for attachment to a tooth or teeth (101) in an intraoral space, comprising:
a housing (107) and/or a retaining plate,
wherein the housing (107) and/or the retaining plate comprises a sensor,
an adhesive region (103) comprising a gutta-percha material (105) for attaching the housing (107) and/or the retaining plate to the tooth (101),
wherein a layer (109) of the gutta-percha material (105) is attached to the housing (107) and/or the retaining plate,
wherein the layer (109) of gutta-percha material (105) is attached to the housing (107) and/or the retaining plate (121) by an adhesive layer (115); and/or the housing (107) and/or the retaining plate comprises a textured surface for attaching the gutta-percha material (105); and/or the housing (107) and/or the retaining plate comprises one or more latching elements for attaching the gutta-percha material (105); and/or the housing (107) and/or the retaining plate comprises one or more connecting elements for establishing a form fit between the adhesive region and the housing (107) and/or the retaining plate (121), and
wherein the gutta-percha material (105) comprises a prefabricated passage opening (111) for guiding fluid from the tooth into an interior of the housing (107).

2. The dental object (100) according to claim 1,
wherein the layer (109) of gutta-percha material (105) has a thickness of 1 μm to 5 mm.

3. The dental object (100) according to claim 1,
wherein the gutta-percha material (105) comprises antibacterial particles or substances.

4. The dental object (100) according to claim 1,
wherein the gutta-percha material (105) comprises a plasticizer.

5. The dental object (100) according to claim 1,
wherein the gutta-percha material (105), the sensor, the housing (107) and/or the retaining plate comprises one or more channels (117) for conducting saliva to a sensor unit.

6. The dental object (100) according to claim 5,
wherein the channels (117) extend obliquely or vertically through the gutta-percha material (105), the sensor, the housing (107) and/or the retaining plate (121).

7. The dental object (100) according to claim 1,
wherein the gutta-percha material (105) is anatomically preformed.

8. The dental object (100) according to claim 1,
wherein the dental object (100) comprises a sensor system, an electronic component and/or a battery.

9. A method of attaching a dental object (100) to a tooth (101) or teeth, comprising the step:

pressing an adhesive region (103) of the dental object (100) comprising a gutta-percha material (105) onto the tooth (101) or teeth,
wherein the dental object (100) comprises a housing (107) and/or a retaining plate,
wherein the housing (107) and/or the retaining plate comprises a sensor,
wherein a layer (109) of the gutta-percha material (105) is attached to the housing (107) and/or the retaining plate,
wherein the layer (109) of gutta-percha material (105) is attached to the housing (107) and/or the retaining plate (121) by an adhesive layer (115); and/or the housing (107) and/or the retaining plate comprises a textured surface for attaching the gutta-percha material (105); and/or the housing (107) and/or the retaining plate comprises one or more latching elements for attaching the gutta-percha material (105); and/or the housing (107) and/or the retaining plate comprises one or more connecting elements for establishing a form fit between the adhesive region and the housing (107) and/or the retaining plate (121), and
wherein the gutta-percha material (105) comprises a prefabricated passage opening (111) for guiding fluid from the tooth into an interior of the housing (107).

10. The method according to claim 9,
wherein the gutta-percha material (105) is heated prior to a press-on.

11. A method of using gutta-percha (105) for attaching a dental object (100) to a tooth (101) or teeth comprising
attaching the dental object (100) to the tooth (101) or teeth using gutta-percha (105),
wherein the dental object (100) comprises a housing (107) and/or a retaining plate,
wherein the housing (107) and/or the retaining plate comprises a sensor,
wherein a layer (109) of the gutta-percha material (105) is attached to the housing (107) and/or the retaining plate (121),
wherein the layer (109) of gutta-percha material (105) is attached to the housing (107) and/or the retaining plate (121) by an adhesive layer (115); and/or the housing (107) and/or the retaining plate comprises a textured surface for attaching the gutta-percha material (105); and/or the housing (107) and/or the retaining plate comprises one or more latching elements for attaching the gutta-percha material (105); and/or the housing (107) and/or the retaining plate comprises one or more connecting elements for establishing a form fit between the adhesive region and the housing (107) and/or the retaining plate (121), and
wherein the gutta-percha material (105) comprises a prefabricated passage opening (111) for guiding fluid from the tooth into an interior of the housing (107).

* * * * *